United States Patent [19]

Hines, Jr.

[11] 3,957,050

[45] May 18, 1976

[54] VENTRICULAR DRAINAGE APPARATUS

[76] Inventor: Robert S. Hines, Jr., 1119 Southwest Ave., Johnson City, Tenn. 37601

[22] Filed: May 23, 1975

[21] Appl. No.: 580,407

[52] U.S. Cl. ............................................. 128/275
[51] Int. Cl.² ................................................ A61F 5/44
[58] Field of Search ........... 128/350, 349, 348, 275, 128/294, 295, 276, 277, 278

[56] References Cited
UNITED STATES PATENTS

| | | | |
|---|---|---|---|
| 3,583,401 | 6/1971 | Vaillancourt | 128/275 |
| 3,604,420 | 9/1971 | Vaillancourt | 128/275 |
| 3,661,143 | 5/1972 | Henkin | 128/275 |
| 3,838,691 | 10/1974 | Paludan et al. | 128/275 |

Primary Examiner—John D. Yasko
Attorney, Agent, or Firm—John R. Walker, III

[57] ABSTRACT

Apparatus for allowing excessive cerebrospinal fluid to drain from within the ventricles of a patient's brain. A hollow tube runs from a typical intraventricular device to a collection bag supported from a base at a selected elevation. The intraventricular device is hollow and is inserted into the ventricles of the patient's brain to allow cerebrospinal fluid to pass from the ventricles of the patient's brain to the intraventricular device, tube and base and into the collection bag. A concentric manometric device is provided to control the pressure of the cerebrospinal fluid passing from the intraventricular device to the collection bag and to allow the patency of the apparatus to be quickly and easily ascertained. Indicia is provided on the base for indicating when the base is properly positioned relative to the ventricles of the patient's brain so that there is no substantial difference in pressure between the collection bag and the ventricles of the patient's brain due to a difference in elevation between the collection bag and the ventricles of the patient's brain.

9 Claims, 3 Drawing Figures

VENTRICULAR DRAINAGE APPARATUS

BACKGROUND OF THE INVENTION

1. Field of the Invention

This invention relates generally to medical devices and more specifically to ventricular drainage apparatuses.

2. Description of the Prior Art

Various medical drainage apparatuses have heretofore been developed. See, for example, Pilling et al. (U.S. Pat. No. 2,140,113); Overment (U.S. Pat. No. 3,312,221); Jinkens et al. (U.S. Pat. No. 3,332,422); Ericson (U.S. Pat. No. 3,478,743); Folkman (U.S. Pat. No. 3,529,599); Huck (U.S. Pat. No. 3,534,738); Vaillancourt et al. (U.S. Pat. No. 3,583,401); Vaillancourt (U.S. Pat. No. 3,604,420); Pashkow (U.S. Pat. No. 3,605,747); Henkin (U.S. Pat. No. 3,661,143); and Paludan (U.S. Pat. No. 3,838,691). None of these prior apparatuses disclose or suggest the present invention. Prior apparatuses and devices for temporarily allowing excessive cerebrospinal fluid to drain from within the ventricles of a patient's brain have been disadvantageous for a number of reasons. The human brain normally produces 250 cc. of cerebrospinal fluid a day. This cerebrospinal fluid normally passes from the ventricles of the brain through various passageways in a manner well known to those skilled in the art. However, sometimes the passage of the cerebrospinal fluid is prevented, resulting in excessive accumulation of cerebrospinal fluid in the ventricles of the brain causing high pressure to be built up in the ventricles. Prior to the present invention, the common method of temporarily relieving this built-up pressure was to insert a typical brain cannula or the like into the ventricles of the brain to allow the cerebrospinal fluid to pass from the ventricles of the brain through the drain cannula into a collection bag or the like generally connected to the brain cannula by a flexible tube. The main disadvantage of this method is the inability to control the pressure of the cerebrospinal fluid and the difficulty of determining the patency of the apparatus. It should be noted that the pressure of the cerebrospinal fluid is extremely critical. More specifically, if the pressure of the cerebrospinal fluid increases too much, herniation of the brain may occur. Likewise, if the pressure decreases too much, shrinkage of the brain may occur. In both cases, permanent injury or death is likely. Thus, a ventricular drainage apparatus which doesn't allow the pressure of the cerebrospinal fluid to be controlled and which doesn't allow its patency to be easily determined is extremely disadvantageous.

To perform satisfactorily, a ventricular drainage apparatus must: (a) be easy to set up and care for; (b) allow easy and quick determination of its patency even in a no-flow or low-flow situation; (c) allow collection of cerebrospinal fluid for laboratory determinations; (d) be a completely closed system to prevent possible infection and contamination; (e) allow the hydrostatic pressure requirement to be changed, especially with reference to maintaining even pressure despite the patient's head position; (f) have anti-backflow characteristics; (g) enable easy sampling of the cerebrospinal fluid and introduction of intraventricular medications; (9) enable easy clearing of the apparatus should it become obstructed; (i) enable easy measurement and drainage of the cerebrospinal fluid in long-term situations; and (j) be able to withstand positional mishandling and to return to correct functioning when placed in the proper position.

SUMMARY OF THE INVENTION

The present invention is directed towards overcoming the problems and disadvantages of prior ventricular drainage apparatuses. The concept of the present invention is to provide a ventricular drainage apparatus which includes means for controlling the pressure of the cerebrospinal fluid passing from the ventricles of a patient's brain to a collection bag. More specifically, the present invention includes, in general, a manometric means having a base member, an outer tube member and an inner tube member. The base member is adapted to be connected to a tube running from an intraventricular device which can be inserted into the ventricles of a patient's brain. The outer tube member includes an opened first end and a closed second end. The first end of the outer tube member is attached to the base member to cause the cerebrospinal fluid passing through the base member from the ventricles of the patient's brain to enter the outer tube member. The inner tube member includes opened first and second ends. The first end of the inner tube member is positioned within the outer tube member to allow the cerebrospinal fluid in the outer tube member to pass into the inner tube member whenever the pressure of the cerebrospinal fluid is sufficient to cause the cerebrospinal fluid in the outer tube member to rise over the first end of the inner tube member. The inner tube member is slidably attached to the base member for allowing the first end of the inner tube member to be selectively positioned within the outer tube member to control the pressure of the cerebrospinal fluid passing from the ventricles of the patient's brain to the inner tube member. The second end of the inner tube member is positioned within a collection bag for receiving and storing the cerebrospinal fluid passing from the ventricles of the patient's brain to the inner tube member.

DESCRIPTION OF THE PREFERRED EMBODIMENT

Figure 1:
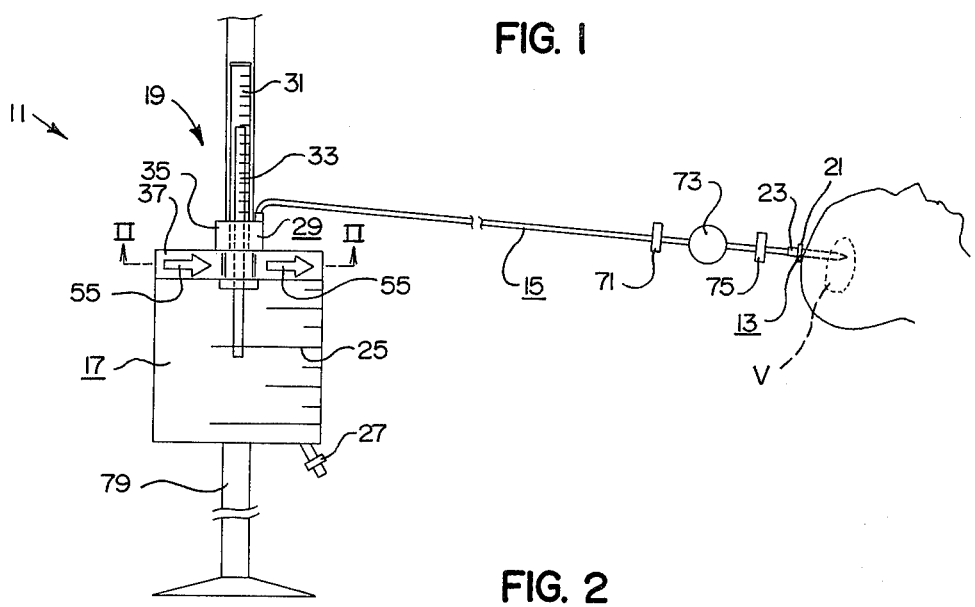
FIG. 1 is an elevational view of the ventricular drainage apparatus of the present invention shown in combination with a patient.
Figure 2:
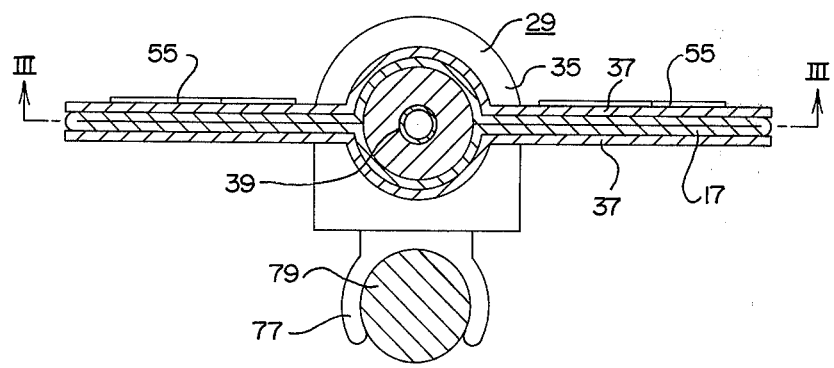
FIG. 2 is a sectional view of a portion of the present invention as taken on line II—II of FIG. 1.
Figure 3:
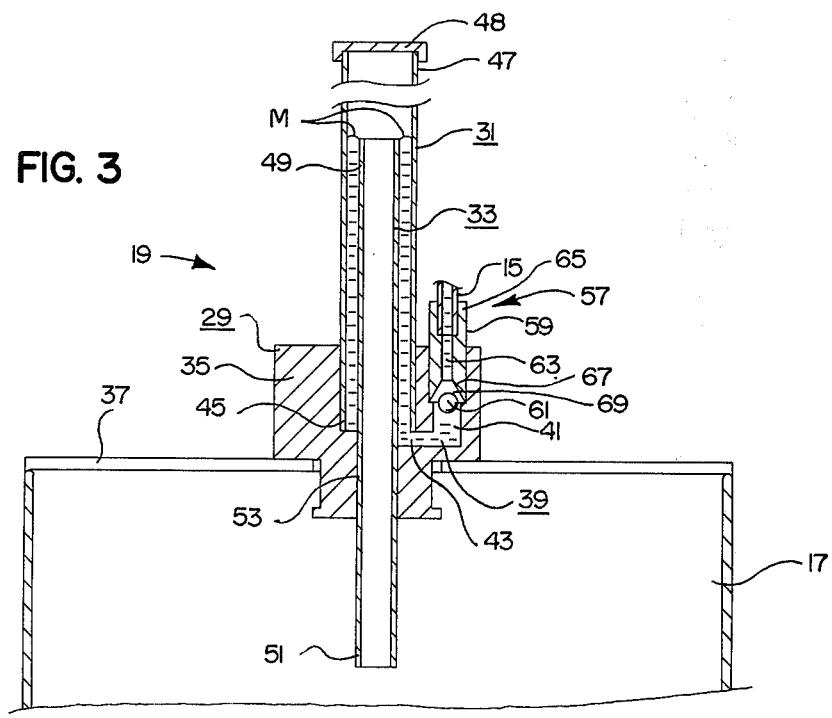
FIG. 3 is a sectional view of a portion of the present invention as taken on line III—III of FIG. 2.

The ventricular drainage apparatus 11 of the present invention is for use in allowing excessive cerebrospinal fluid to drain from within the ventricles V of a patient's brain. The ventricular drainage apparatus 11 includes, in general, an intraventricular means or device 13, a tube 15, a collection bag 17 and a manometric means 19.

The intraventricular device 13 is for insertion into the ventricles V of a patient's brain and is well known to those skilled in the art. More specifically, the intraventricular device 13 may be a brain cannula such as a Scott or Siletz cannula well known to those skilled in the art. The intraventricular device 13 preferably includes a connecting portion 21 to allow the tube 15 to be securely connected to the intraventricular device 13. Preferably, the connecting portion 21 is a Leur-type connecting member well known to those skilled in the art.

The tube 15 is preferably of the type used in intravenous applications and is well known to those skilled in the art. More specifically, the tube 15 is preferably of a flexible plastic material of a substantially small diameter. The tube 15 includes a connecting portion 23 on one end thereof for coacting with the connecting portion 21 of the intraventricular device 13. The connecting portion 23 is preferably a Leur-type connecting member well known to those skilled in the art.

The collection bag 17 is preferably constructed of an expandable and flexible material such as vinyl plastic. The collection bag 17 is preferably transparent and provided with indicia 25 to allow the amount of cerebrospinal fluid stored therein to be determined. The collection bag 17 is preferably provided with a closable drain port 27 for allowing selective removal of the cerebrospinal fluid therefrom.

The manometric means 19 includes a base member 29, an outer tube member 31 and an inner tube member 33. The base member 29 preferably includes a body portion 35 and bag support portions 37. The body portion 35 includes a passageway 39. The passageway 39 has a first end 41 for communication with the tube 15 and a second end 43 for communication with the outer tube member 31. The outer tube member 31 includes an opened first end 45 and a closed second end 47. The second end 47 is preferably closed by means of a cap 48. The opened first end 45 of the outer tube member 31 is attached to the body portion 35 of the base member 29 adjacent the second end 43 of the passageway 39 in a manner to allow communication therebetween. The inner tube member 33 includes opened first and second ends 49, 51 and a midportion 53. The opened first end 49 of the inner tube member 33 is positioned within the outer tube member 31. The opened second end 51 of the inner tube member 33 is positioned within the collection bag 17. The midportion 53 of the inner tube member 33 is slidably attached to the body portion 35 of the base member 29 for allowing the first end 49 of the inner tube member 33 to be selectively positioned within the outer tube member 31. The manometric means 19 preferably includes indicia portions for indicating when the base member 29 is properly positioned relative to the ventricles V of the patient's brain. More specifically, the bag support portions 37 of the base member 39 are preferably provided with arrow-like portions 55 for reasons which will become apparent hereinafter. The arrow-like portions 55 are preferably of a contrasting color relative to the bag support portions 37 and may be raised from or recessed into the bag support portions 37.

The ventricular drainage apparatus 11 preferably includes valve means 57 intermediate the intraventricular device 13 and the manometric means 19 for preventing cerebrospinal fluid from passing from the collection bag 17 to the intraventricular device 13. The valve means 57 includes a body member 59 and a ball member 61. The body member 59 includes a passageway 63 having opened first and second ends 65, 67. The body member 59 of the valve means 57 is preferably mounted to the body portion 35 of the base member 29 of the manometric means 19 with the passageway 63 of the valve means 59 in communication with the passageway 39 of the base member 29. The first end 65 of the passageway 63 is preferably attached to the tube 15. The second end 67 of the passageway 63 is provided with a valve seat portion 69. The ball member 61 of the valve means 57 is adapted to coact with the valve seat portion 69 to close the passageway 63. The ball member 61 is constructed of a substance such as plastic having a specific gravity less than the specific gravity of the cerebrospinal fluid. The ball member 61 is movably positioned in the first end 51 of the passageway 39 in the base member 29 of the manometric means 19. When the cerebrospinal fluid in the passageway 39 is in a static condition, the ball member 61 will float against the valve seat portion 69 to prevent the cerebrospinal fluid from passing from the manometric means 19 to the intraventricular device 13.

The ventricular drainage apparatus 11 of the present invention preferably includes clamp means 71 for selectively preventing the cerebrospinal fluid from draining from within the ventricles V of the patient's brain. The clamp means 71 is preferably positioned in the tube 15 intermediate the intraventricular device 13 and manometric means 19. The clamp means 71 may be of any type well known to those skilled in the art.

The ventricular drainage apparatus 11 preferably includes means for providing a quantity of compressed fluid to the tube 15, valve means 57 and manometric means 19 to clear any possible clogging thereof. The means for providing a quantity of compressed fluid preferably consists of a rubber squeeze bulb 73. It should be noted that when the squeeze bulb 73 is used to clear the tube 15, valve means 57 and/or manometric means 19, the tube 15 should be clamped intermediate the squeeze bulb 73 and intraventricular device 13 by a clamp 75 to prevent the quantity of compressed fluid from passing from the squeeze bulb 73 to the intraventricular device 13. The squeeze bulb 73 should have properties that enable it to be used as an injection site for the administration of intraventricular medication. That is, the squeeze bulb 73 should be constructed in a manner well known to those skilled in the art so that medication can be injected into the cerebrospinal fluid in the tube 15. The medication can be introduced into the ventricles V of the patient's brain by simply closing the clamp 71 in the tube 15 and squeezing the squeeze bulb 17 to force the medication from the tube 15 through the intraventricular device 13 and into the ventricles V of the patient's brain.

The ventricular drainage apparatus 11 of the present invention preferably includes a clamp portion 77 for clamping the collection bag 17 and the manometric means 19 to a stand 79 such as a typical intravenous stand 79.

The operation of the ventricular drainage device 11 of the present invention is quite simple. The intraventricular device 13 is inserted into the ventricles V of the patient's brain in a manner well known to those skilled in the art. The tube 15 is then connected to the intraventricular device 13 by means of the connecting portions 21, 23. The manometric means 19 is adjusted vertically on the stand 79 until the arrow-like portions 55 are level with the ventricles V of the patient's brain thereby insuring that the manometric means 19 is positioned at the proper height relative to the the ventricles V of the patient's brain so that proper hydrostatic pressure is provided despite the patient's head position. With the clamps 71, 75 open, cerebrospinal fluid will pass from the ventricles V of the patient's brain, through the intraventricular device 13, tube 15, valve means 57 and manometric means 19 into the collection bag 17. The first end 49 of the inner tube member 33 may be adjusted to different heights within the outer tube member 31 to control the pressure of the cerebrospinal fluid passing from the ventricles V of the patient's brain to the collection bag 17. That is, once the cerebrospinal fluid enters the outer tube member 31, it travels up within the outer tube member 31 until it reaches the opened first end 49 of the inner tube member 33. By varying the position of the inner tube member 33 within the outer tube member 31 the amount of pressure the cerebrospinal fluid must exert to reach the opened first end 49 of the inner tube member 33 is varied. Upon reaching the opened first end 49 of the inner tube member 33, the cerebrospinal fluid forms a meniscus M between the outer and inner tube members 31, 33. This meniscus formation is one of the most important principles of this invention. That is, the meniscus formation allows the normal cerebrospinal fluid pulsations to be noted and thereby allows the patency of the ventricular drainage apparatus 11 to be easily and quickly ascertained even in situations where the production of cerebrospinal fluid is at a minimum or in a low flow situation. It will be understood that the manipulation of inner tube 33 to adjust the first end 49 thereof may be accomplished manually from outside bag 17 since the lower end 51 may be grasped and manipulated through the flexible bag 17.

As thus constructed and operated, the present invention provides a ventricular drainage apparatus which allows the pressure of the cerebrospinal fluid passing from the ventricles of a patient's brain to a collection bag to be controlled and allows the patency of the drainage apparatus to be quickly ascertained.

Although the invention has been described and illustrated with respect to a preferred embodiment thereof, it is not to be so limited since changes and modifications may be made therein which are within the full intended scope of the invention.

I claim:

1. A ventricular drainage apparatus for positioning intermediate an intraventricular means for insertion into the ventricles of a patient's brain to allow cerebrospinal fluid to pass from the ventricles of the patient's brain and a collection bag means for collecting and storing the cerebrospinal fluid, to control the pressure of the cerebrospinal fluid passing from the intraventricular means to the collection bag; said ventricular drainage apparatus comprising an outer tube member and an inner tube member, said outer tube member having an opened first end and a closed second end, said first end communicating with the intraventricular means for allowing the cerebrospinal fluid to pass into said outer tube member, said inner tube member having an opened first end and an opened second end, said first end being slidably positioned within said outer tube member for allowing the cerebrospinal fluid to pass from said outer tube member into said inner tube member, said second end being positioned within the collection bag means for allowing the cerebrospinal fluid to pass from said inner tube member into the collection bag means when the pressure of the cerebrospinal fluid is sufficient to cause the cerebrospinal fluid in said outer tube member to rise above said first end of said inner tube member.

2. A ventricular drainage apparatus for allowing excessive cerebrospinal fluid to drain from within the ventricles of a patient's brain, said drainage apparatus comprising:

a. intraventricular means for insertion into the ventricles of the patient's brain to allow cerebrospinal fluid to pass from the ventricles of the patient's brain;

b. tube means for receiving the cerebrospinal fluid from said intraventricular means;

c. collection bag means for collecting and storing the cerebrospinal fluid; and d. manometric means for positioning intermediate said intraventricular means and said collection bag and for controlling the pressure of the cerebrospinal fluid passing from said intraventricular means to said collection bag means, said manometric means including an outer tube member and an inner tube member, said outer tube member having an opened first end and a closed second end, said first end communicating with said tube means for allowing the cerebrospinal fluid to pass into said outer tube member, said inner tube member having an opened first end and an opened second end, said first end being slidably positioned within said outer tube member for allowing the cerebrospinal fluid to pass from said outer tube member into said inner tube member, said second end being positioned within said collection bag means for allowing the cerebrospinal fluid to pass from said inner tube member into said collection bag means when the pressure of the cerebrospinal fluid is sufficient to cause the cerebrospinal fluid in said outer tube member to rise above said first end of said inner tube member.

3. The ventricular drainage apparatus of claim 2 in which said manometric means includes indicia portions for indicating when said manometric means is properly positioned relative to the ventricles of the patient's brain.

4. A ventricular drainage apparatus for allowing excessive cerebrospinal fluid to drain from within the ventricles of a patient's brain, said drainage apparatus comprising:

a. intraventricular means for insertion into the ventricles of the patient's brain, said intraventricular means including a first end and a second end, said first end being adapted to be inserted into the ventricles of the patient's brain, said intraventricular means including a passageway extending between said first and second ends for allowing cerebrospinal fluid to pass from the ventricles of the patient's brain and through said intraventricular means;

b. tube means for receiving the cerebrospinal fluid from said intraventricular means, said tube means including a first end and a second end, said first end being attached to said second end of said brain cannula, said tube means including a passageway extending between said first and second ends for allowing cerebrospinal fluid to pass from said brain cannula and into said tube means;

c. collection bag means for receiving and storing the cerebrospinal fluid after the cerebrospinal fluid passes through said tube means, said collection bag means being adapted to expand as the cerebrospinal fluid is received and stored therein;

d. manometric means positioned intermediate said intraventricular device and said collection bag means for controlling the pressure of the cerebrospinal fluid passing from said intraventricular means to said collection bag means, said manometric means including a base means having a bag support portion for supporting said collection bag means and having a body portion including a passageway for allowing the cerebrospinal fluid to pass through said base means, said passageway having a first end and a second end, said manometric means including an outer tube member and an inner tube member, said outer tube member having an opened first end and a closed second end, said first end being attached to said body portion of said base means adjacent said second end of said passageway for allowing the cerebrospinal fluid to pass from said base means into said outer tube member, said inner tube member having an opened first end and an opened second end, said first end being slidably positioned within said outer tube member for allowing the cerebrospinal fluid to pass from said outer tube member into said inner tube member, said second end extending through said base means and being positioned within said collection bag means for allowing the cerebrospinal fluid to pass from said inner tube member into said collection bag means when the pressure of the cerebrospinal fluid is sufficient to cause the cerebrospinal fluid in said outer tube to rise above said first end of said inner tube member; and e. valve means for preventing cerebrospinal fluid from passing from said collection bag means to said intraventricular means, said valve means including a body member having first and second ends with a valve seat portion adjacent said second end, said first end being attached to said second end of said tube means and said second end being attached to said first end of said passageway of said base means of said manometric means, said body member including a passageway extending between said first and second ends for allowing cerebrospinal fluid to pass from said collection bag means to said base means, said valve means including a ball member for coacting with said valve seat portion of said body member to prevent cerebrospinal fluid from passing from said collecting bag means to said brain cannula, said ball member being constructed of a substance having a specific gravity less than the specific gravity of the cerebrospinal fluid for causing said ball member to be floated against said valve seat portion of said valve means thereby preventing the cerebrospinal fluid from passing from said collection bag means to said brain cannula.

5. The ventricular drainage apparatus of claim 4 in which said base means of said manometric means includes indicia portions for indicating when said base means is properly positioned relative to the ventricles of the patient's brain.

6. The ventricular drainage apparatus of claim 5 in which is included clamp means for selectively preventing the cerebrospinal fluid from draining from within the ventricles of the patient's brain, said clamp means being positioned in said tube means intermediate said first and second ends thereof.

7. The ventricular drainage apparatus of claim 6 in which is included means for providing a quantity of compressed fluid to said tube means, said valve means and said manometric means to clear any possible clogging thereof.

8. The ventricular drainage apparatus of claim 7 in which is included means for allowing medication to be injected into the cerebrospinal fluid in said tube means and for allowing samples of the cerebrospinal fluid to be withdrawn from said tube means.

9. The ventricular drainage apparatus of claim 8 in which said collection bag means includes a closable drain port for allowing selective removal of the cerebrospinal fluid therefrom.

* * * * *